(12) United States Patent
Kaneyama et al.

(10) Patent No.: US 9,370,375 B2
(45) Date of Patent: Jun. 21, 2016

(54) ARTIFICIAL KNEE JOINT AND SURGICAL INSTRUMENT USED IN ARTIFICIAL KNEE JOINT REPLACEMENT SURGERY

(75) Inventors: Ryutaku Kaneyama, Kisarazu (JP); Kouichi Kuramoto, Okayama (JP); Keitarou Yamamoto, Okayama (JP); Daisuke Maruyama, Okayama (JP)

(73) Assignees: NAKASHIMA MEDICAL CO., LTD., Okayama-Ken; Ryutaku Kaneyama, Chiba-Ken ( * ) Notice: Subject to any disclaimer, the term of this patent is extended or adjusted under 35 U.S.C. 154(b) by 261 days.

(21) Appl. No.: 14/001,038

(22) PCT Filed: Oct. 21, 2011

(86) PCT No.: PCT/JP2011/074889
§ 371 (c)(1),
(2), (4) Date: Nov. 4, 2013

(87) PCT Pub. No.: WO2012/114580
PCT Pub. Date: Aug. 30, 2012

(65) Prior Publication Data
US 2014/0058398 A1     Feb. 27, 2014

(30) Foreign Application Priority Data
Feb. 24, 2011  (JP) .................................. 2011-037905

(51) Int. Cl.
*A61B 17/16* (2006.01)
*A61B 17/15* (2006.01)
*A61F 2/38* (2006.01)
*A61F 2/46* (2006.01)
(Continued)

(52) U.S. Cl.
CPC ........... *A61B 17/1675* (2013.01); *A61B 17/155* (2013.01); *A61F 2/3836* (2013.01); *A61F 2/4684* (2013.01); *A61B 17/154* (2013.01); *A61B 17/1764* (2013.01); *A61F 2/3859* (2013.01); *A61F 2/4657* (2013.01); *A61F 2002/30604* (2013.01); *A61F 2002/30607* (2013.01); *A61F 2002/3895* (2013.01); *A61F 2002/4661* (2013.01)

(58) Field of Classification Search
CPC .......................... A61B 17/154; A61B 17/155
See application file for complete search history.

(56) References Cited

U.S. PATENT DOCUMENTS 5,258,032 A    11/1993  Bertin
5,735,904 A     4/1998  Pappas (Continued)

FOREIGN PATENT DOCUMENTS

JP    H7-507946    9/1995
JP    H7-508203    9/1995

(Continued)

*Primary Examiner* — Andrew Yang
(74) *Attorney, Agent, or Firm* — DLA Piper LLP (US)

(57) ABSTRACT

A surgical instrument including a pre-cut trial mounted on a pre-cut line which is cut shallower than a genuine-cut line. The pre-cut trial is modeled after the genuine implant which is mounted on resected surfaces formed by performing genuine-cutting and comprised of an end resected surface, posterior and anterior resected surfaces, and posterior and anterior chamfer-resected surfaces on the distal end of a femur, and the pre-cut trial is mounted on the pre-cut line, thus observing the extended and flexed positions of the femur and the state of flexion thereof so as to make judgment if the genuine implant is appropriate.

7 Claims, 22 Drawing Sheets

(51) Int. Cl.
*A61F 2/30* (2006.01)
*A61B 17/17* (2006.01)

(56) References Cited

U.S. PATENT DOCUMENTS 6,916,324 B2 * 7/2005 Sanford ............... A61B 17/155
606/87

2004/0153086 A1 8/2004 Sanford
2004/0153087 A1 8/2004 Sanford et al.

FOREIGN PATENT DOCUMENTS

| JP | H10-137273 | 5/1998 |
| JP | P2007-075517 A | 3/2007 |
| JP | P2012-055597 A | 3/2012 |
| WO | WO 96/25123 | 8/1996 |

* cited by examiner

ARTIFICIAL KNEE JOINT AND SURGICAL INSTRUMENT USED IN ARTIFICIAL KNEE JOINT REPLACEMENT SURGERY

TECHNICAL FIELD

The present invention relates to an artificial knee joint, that is, an artificial knee joint consisting of a genuine implant and a pre-cut trial which is mounted before the genuine implant is mounted for observing the state of extension and flexion of the knee joint and to a surgical instrument used in surgical operations for replacing artificial knee joints.

BACKGROUND TECHNOLOGY

When the knee joint is affected by osteoarthritis, rheumatoid arthritis, or bone tumors or suffers a trauma, etc., the parts of the joint which are damaged, including the end portions of the femur and tibia, are resected, and an artificial knee joint replacement is mounted. As conventionally seen, an artificial knee joint consists of a combination of two femoral side members, corresponding to the medial and lateral condyles, and tibial side members, corresponding to the joint surfaces which receive the two femoral side members in such a way that they can rotate; and, artificial knee joints constructed with these femoral side members and tibial side members should perform the same movements as the body's original knee joint.

The femur and tibia are connected by many ligaments, and their extension and flexion are caused by ligaments that contracts and relaxes. In contraction, particularly, it is desirable for the same tensile force to be produced for extension and flexion, and the joint must work smoothly, without causing any pain in flexing. Especially for Japanese people who frequently sit on the floor with their legs folded underneath in Japanese style, it is necessary that more than 90° of flexion be possible. In view of the above, in the bone resection instrument proposed in Patent Reference 1, referred to below, it is confirmed that there is the same tensile force in both the extended and flexed positions, and then the bone resection range is determined.

However, the invention of this prior art confirms (measures) the tensile forces of the ligaments in the extended and flexed positions. Accordingly, the surgical operations are troublesome and require a long time. Moreover, the structure is complicated and has many movable parts and adjustment parts, and thus many operations which are laborious and require skill are needed. Furthermore, this instrument is heavy an d expensive.

Therefore, the inventors of the present application have proposed Patent Reference 2 referred to below. This is an instrument that is used when the distal end of femur is resected, and it is, fundamentally, a bone resection instrument which has a very simple structure, consisting of three parts, and it is simple to operate. It is characterized by the fact that the resection can be performed accurately along a pre-set line. However, even though resection is performed accurately along the pre-set line, problems would arise when actual artificial knee joint is mounted. Moreover, it is difficult to obtain an accurate understanding of the behavior of the joint when the joint is flexed from the extended position to the flexed position.

PRIOR ART

Patent References

Patent Reference 1: Japanese Patent Application Laid-Open No. 2007-075517

Patent Reference 2: Japanese Patent Application No. 2010-203873, Specification

SUMMARY OF THE INVENTION

Problems the Invention Attempts to Solve

The present invention provides a further improvement to a femur side bone resection instrument of Patent Reference 2 referred to in the above, and in the present invention, before a legitimate femur-side artificial joint (genuine implant) is mounted, a pre-cut trial which is modeled after the legitimate femur-side artificial joint is mounted to the femur, and the gap between the pre-cut trial and the tibial side resected surface at the extended position and flexed position and during the movement from the extended position to the flexed position and also the behavior of the femoral side and tibial side members are measured and observed, so that it can be judged whether the genuine implant which has been mounted is appropriate or not. Moreover, in the present invention, healthy bones are preserved as much as possible, and the operation time is made shortened, thus reducing the burden of the patient. Furthermore, the present invention provides a surgical instrument which has a comparatively simple structure and is easily operated and an artificial knee joint which is mounted when an operation is performed with this instrument.

Means to Solve the Problems

In view of the problems above, the present invention provides an artificial knee joint which is characterized by the fact that it is an artificial knee joint in which a smooth-surfaced pre-cut trial is included, and this pre-cut trial is, when an artificial knee joint replacement operation is performed, mounted, at least part thereof, on an end resected surface of a pre-cut line, which is cut more shallower than a genuine cut line, by inserting a pin in the end resected surface, so that the extension and flexion of the femur and tibia are observed and that it is judged whether or not the genuine-cut line and the genuine implant are appropriate, the pre-cut trial being mounted before a smooth-surfaced genuine implant of the femur side is, by inserting a pin in the end resected surface, mounted along a resected surface which is obtained by genuine-cutting (regular-cutting) the distal end of the femur and comprised of an resected surface, which is perpendicular to the bone axis, posterior and anterior resected surfaces, which are parallel to the bone axis, a posterior chamfer-resected surface connecting the end resected surface and the posterior resected surface, and an anterior chamfer-resected surface connecting the end resected surface and the anterior resected surface; and this pre-cut trial is mounted on part or all of the above-described genuine-cut line or part or all of the pre-cut line.

The present invention provides, as manners of mounting the pre-cut trial, an artificial knee joint in which the pre-cut trial is mounted on the end resected surface of made along the genuine-cut line and also mounted on one or two or more of the posterior chamfer-resected surface, the posterior resected surface, the anterior chamfer-resected surface and the anterior resected surface, and among these surface, at least one is a pre-cut line; and further in the present invention an artificial knee joint is provided in which the pre-cut trial is mounted on the end resected surface of made along the pre-cut line and also on one or two or more of the posterior chamfer-resected surface, the posterior resected surface, the anterior chamfer-resected surface and the anterior resected surface of made along the genuine-cut line or the pre-cut line.

Moreover, the present invention provides, as a surgical instrument for bone resection in order to mount an artificial knee joint that includes a pre-cut trial, a surgical instrument in which the pre-cut guide is mounted on the end resected surface, the pre-cut guide being fixed to the end resected surface, defined by the genuine-cut line or the pre-cut line, by using as a guide a pre-cut guide guide-pin which is inserted in the end resected surface through an insertion hole formed in a femoral sizer which is seated in and fitted to the anterior and posterior condyles of the femur, a resection instrument is inserted from an insertion hole, and at least the posterior chamfer-resected surface and posterior resected surface are formed by performing genuine-cut or pre-cut by inserting a resecting instrument into the insertion hole; and further the present invention provides a surgical instrument in which the pre-cut guide has an insertion hole through which a resection instrument for cutting the anterior chamfer-resected surface and anterior resected surface can be inserted to perform genuine-cut or pre-cut.

Furthermore, the present invention provides a surgical instrument further including a genuine-cut guide that is mounted on the end resected surface, wherein after the pre-cut trial is mounted and the states in the extended and flexed positions and the flexing state are observed, a spacer block is inserted between the end resected surface of the genuine-cut line or the pre-cut line and the end resected surface of the tibial side, and the genuine-cut guide is fixed to the end resected surface by using as a guide a genuine-cut guide guide-pin which is inserted into the end resected surface through an insertion hole of the genuine-cut guide guide-pin guide, which is attached to the spacer block and fitted to the end resected surface of the genuine-cut line or pre-cut line, so that a resection instrument is inserted through the insertion hole so as to perform genuine-cut.

In addition, the present invention provides a surgical instrument in which the insertion hole of the genuine-cut guide guide-pin guide is a hole into which a hole-making instrument, such as a drill, can be inserted, and the genuine-cut guide has a sleeve which can be inserted in the instrument hole formed by the hole-making instrument and has a hole in it into which the genuine-cut guide guide-pin can be inserted, and the genuine-cut guide is fixed to the end resected surface which is formed by genuine-cut or pre-cut using this sleeve. The present invention further provides a surgical instrument in which the insertion hole of the femoral sizer is one into which a hole-making instrument such as a drill can be inserted, and the pre-cut guide-pin is inserted into the instrument hole formed by this hole-making instrument.

Effect of the Invention

According to the present invention, the gap between the tibia and the end resected surface is measured in the extended position and the flexed position and during flexion; and the states of the extended and flexed positions and the behavior from the extended position to the flexed position are observed; and as a result, it can be judged whether or not the previously set-up genuine implant and the cut lines are appropriate. Therefore, the genuine implant which is mounted after this can be mounted in the most appropriate state for the patient. Because of this respect, the pre-cut line is as close as possible to the genuine-cut line, and the pre-cut trial is also as close to the genuine implant as possible. As a manner of mounting the pre-cut trial, in the present invention, the pre-cut trial is fitted to the end resected surface of the genuine-cut line or the pre-cut line, and the pre-cut trial is further fitted to any or all of the other posterior chamfer-resected surface, posterior resected surface, anterior chamfer-resected surface, and anterior resected surface, and at least one of these is a pre-cut resected surface.

According to the surgical instrument of the present invention, the resection of the various resected surfaces on which the pre-cut trial is mounted can be easily and accurately performed. In addition to the above, according to the surgical instrument of the present invention, the pre-cut trial can also be mounted on the anterior side of the condyles, and it be made closer to the genuine implant. By means of the surgical instrument of the present invention, the resection of the surfaces by the pre-cut can be done easily and accurately. According to the surgical instrument of the present invention, a spacer block and a genuine-cut guide guide-pin are made unnecessary, and the operation time can be shortened. According to the surgical instrument of the present invention, the insertion of the pre-cut guide guide-pin is facilitated, and cracks are not produced the insertion location.

MODES FOR CARRYING OUT THE INVENTION

Figure 1:
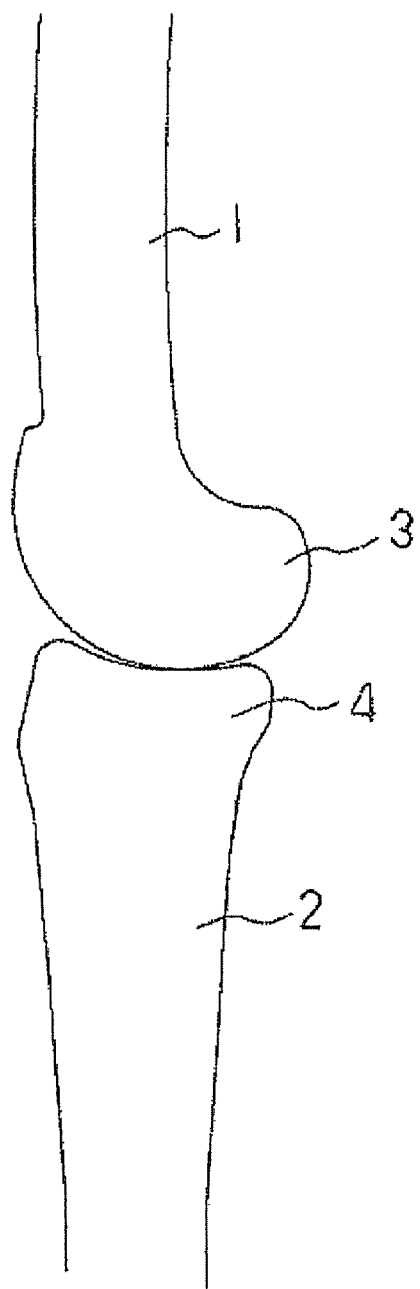
FIG. 1: Side view showing a relationship between the femur and the tibia.
Figure 2:
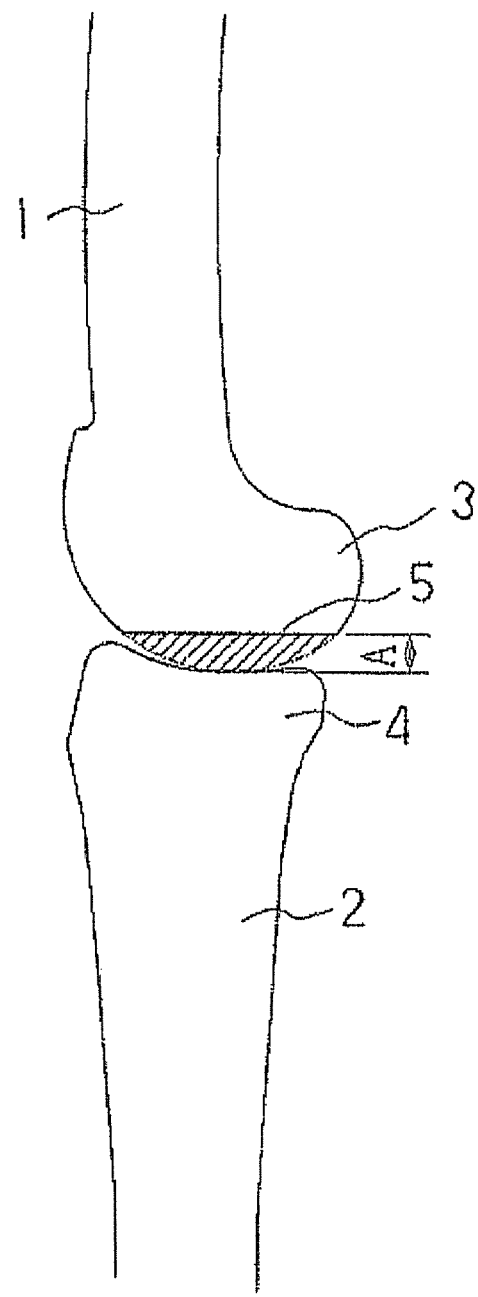
FIG. 2: Side view showing a relationship between the femur and the tibia.

An embodiment of the present invention will be described below according to the sequence of surgical procedure and with reference to the drawings. FIG. 1 is a side view of the femur 1 and tibia 2 when they are in the extended position. The distal end of the femur takes the shape of knobs, known as "condyles 3", which project anteriorly, posteriorly, laterally and medially; and the proximal end of the tibia 2 has an articular surface 4 which receives the condyles 3 in such a way that they can rotate. There are two condyles 3 and two articular surfaces 4 on the left and right. FIG. 2 is a side view of a case in which the distal ends of the condyles 3 which have been damaged are, when an artificial knee joint replacement is performed, resected for the resection range A (indicated by diagonal lines). The lower end of the resection range A, in the extended position of the femur, is a flat (perpendicular to the axis of the bone) femoral distal end resected surface 5 (referred to below as an "end resected surface").

Figure 3:
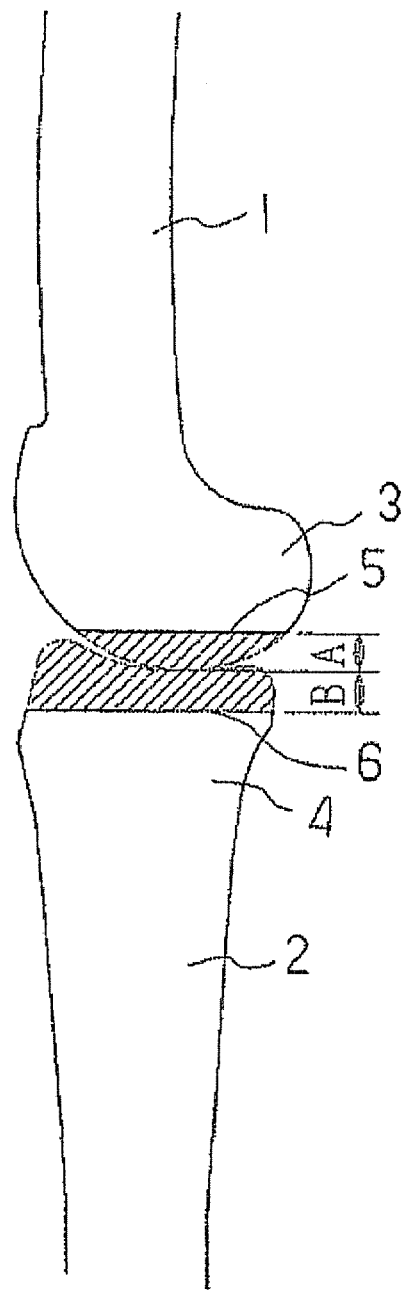
FIG. 3: Side view showing a relationship between the femur and the tibia.
Figure 4:
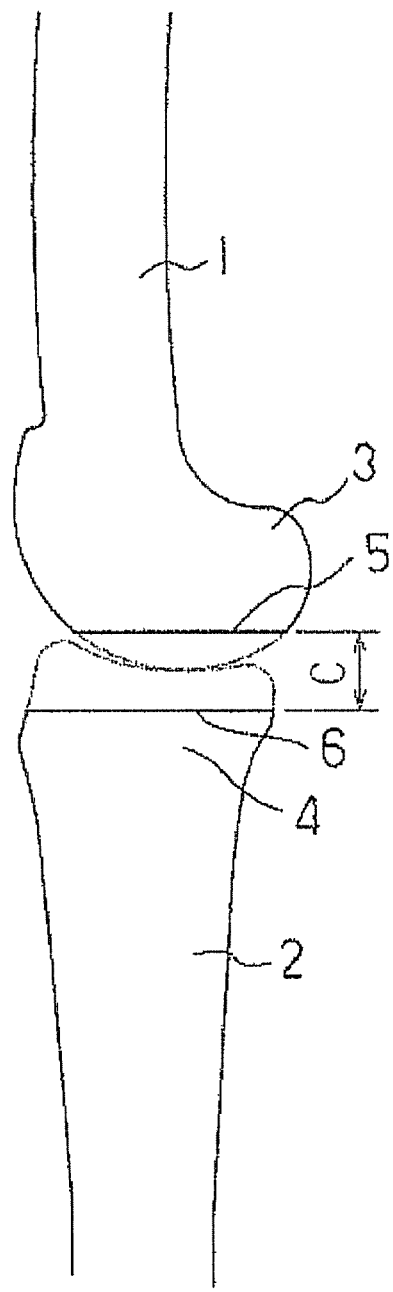
FIG. 4: Side view showing a relationship between the femur and the tibia.

In the same manner, the proximal end of the articular surface 4 of the tibia 2 is resected in the resection range B (shown by diagonal lines), as shown in FIG. 3. In this case, the upper end of the resection range B is a flat tibial proximal end resected surface 6 (referred to below as an "end resected surface"). Accordingly, in the extended position of the femur and tibia, the end resected surfaces 5 and 6 are parallel to each other and horizontal. FIG. 4 shows the resection range C which is A+B. These resection ranges A and B are determined by the physician so as to correspond to a genuine implant, which is to be mounted, by judging the degree of injury to the knee joint, the patient's age, the bone structure, bone substance, etc.

Figure 5:
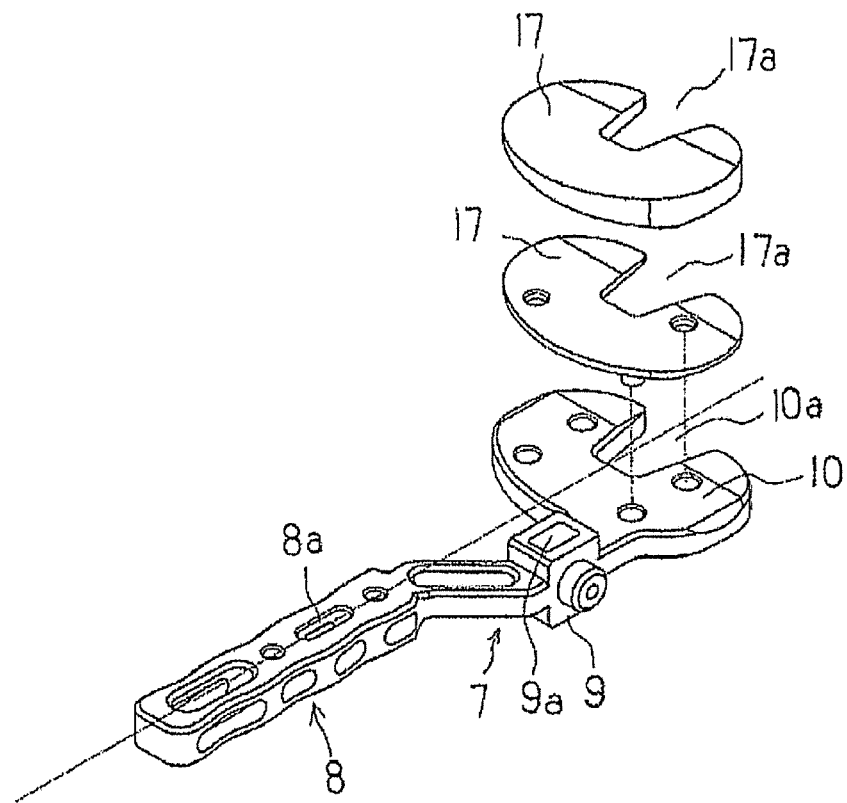
FIG. 5: Perspective view of a spacer block.
Figure 6:
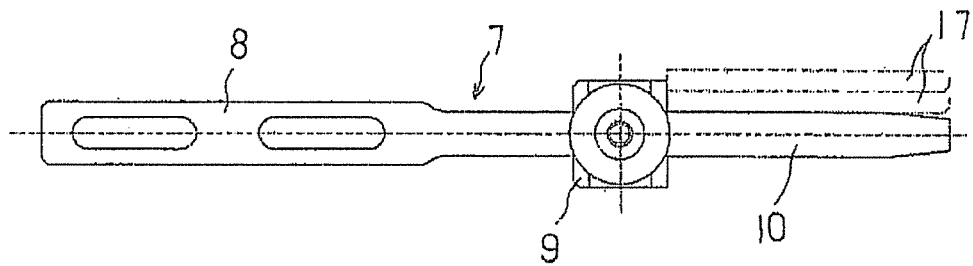
FIG. 6: Side view of the spacer block.
Figure 7:
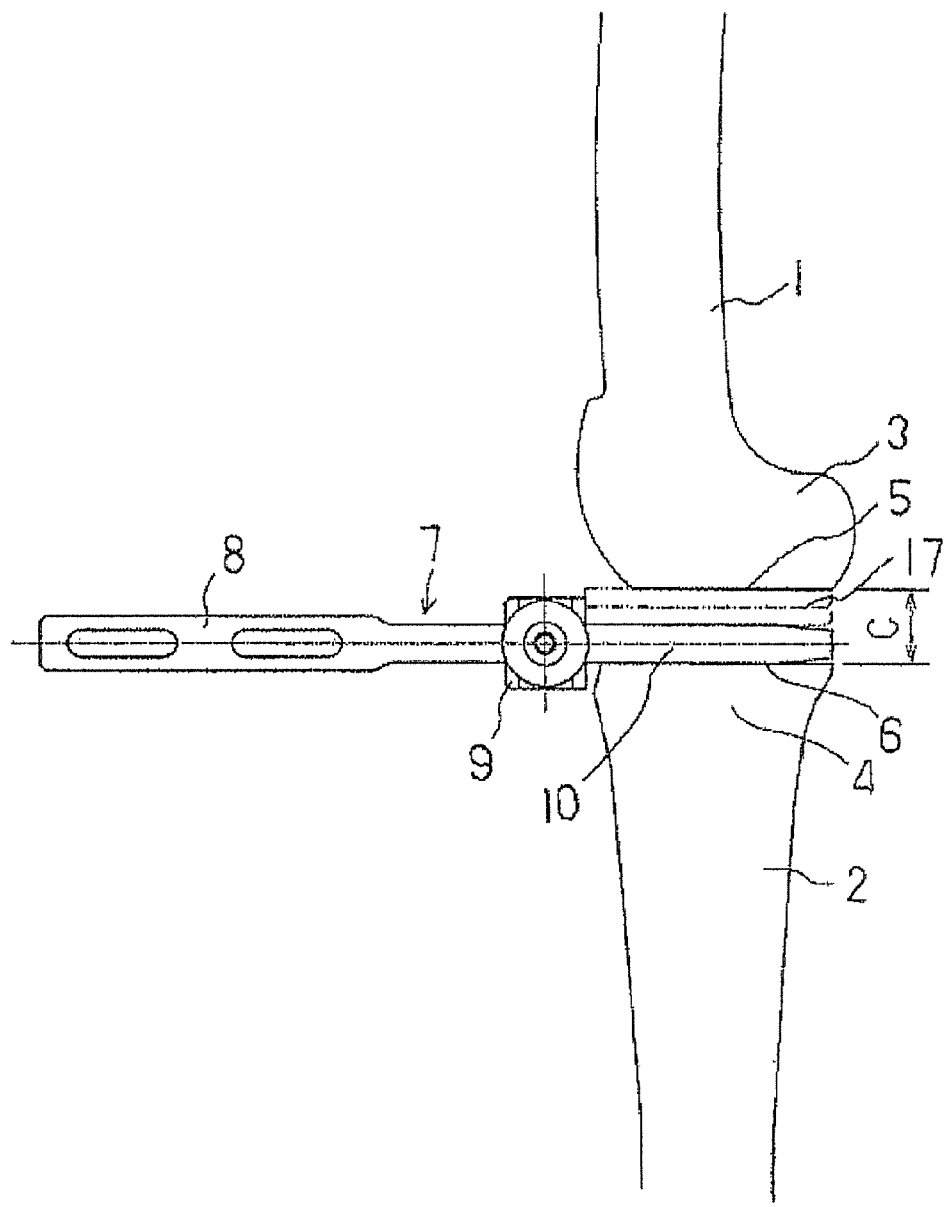
FIG. 7: Side view in which the spacer block is inserted between resected surfaces.

FIGS. 5 to 7 show a spacer block 7. The spacer block 7 is inserted between the end resected surfaces 5 and 6 in order to verify the resection range C in the extended position of the femur and tibia. The spacer block 7 is comprised, from the near side, of a grip 8, a hollow box 9 which has a perpendicular vertical hole 9a, and a reference spacer part 10. Since there is a protuberance in the center of articular surface, a cut-out 10a is formed in the central front face of the reference spacer part 10 in order to accommodate it (the same is true for the adjustment spacer described below). Among these parts, the grip 8 is a handle held by the operator, and a plurality of vertical holes 8a used for alignment with a lower limb are formed in the center of it. The vertical hole 9a of the hollow box 9 is for inserting therein a genuine-cut guide guide-pin guide (referred to below as a "genuine-cut pin guide") 11 described below, and it is shaped as a square hole, so that the genuine-cut pin guide 11 does not rotate.

In the above structure, the axis center of the grip 8 passes through the center of the reference spacer part 10. However, since the hollow box 9 is set immediately in front of the knee joint in order to increase the ability of aligning the genuine-cut pin guide 11 which is mounted in the hollow box, the area surrounding the hollow box 9 of the grip 8 is set off from the axis center, so that the patellar tendon is held in a position which will not obstruct the observation and operations (the patellar tendon is held eccentrically outside). Accordingly, the genuine-cut pin guide 11 is eccentric toward the axis center with respect to its leg 11a; and when the leg 11a is inserted into the vertical hole 9a, the genuine-cut pin guide 11 faces the reference spacer part 10 in alignment therewith.

Figure 8:
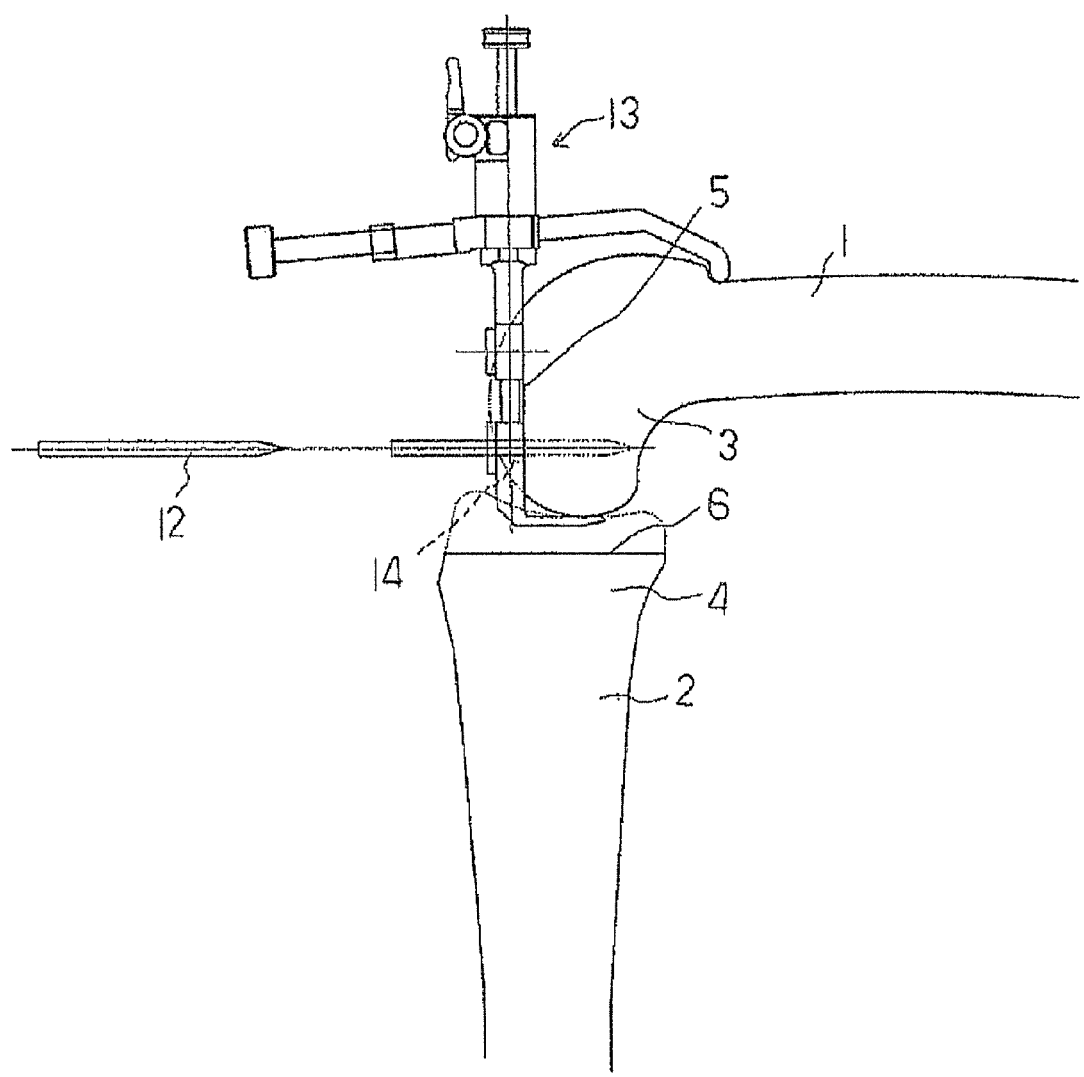
FIG. 8: Side view of a femoral sizer.
Figure 9:
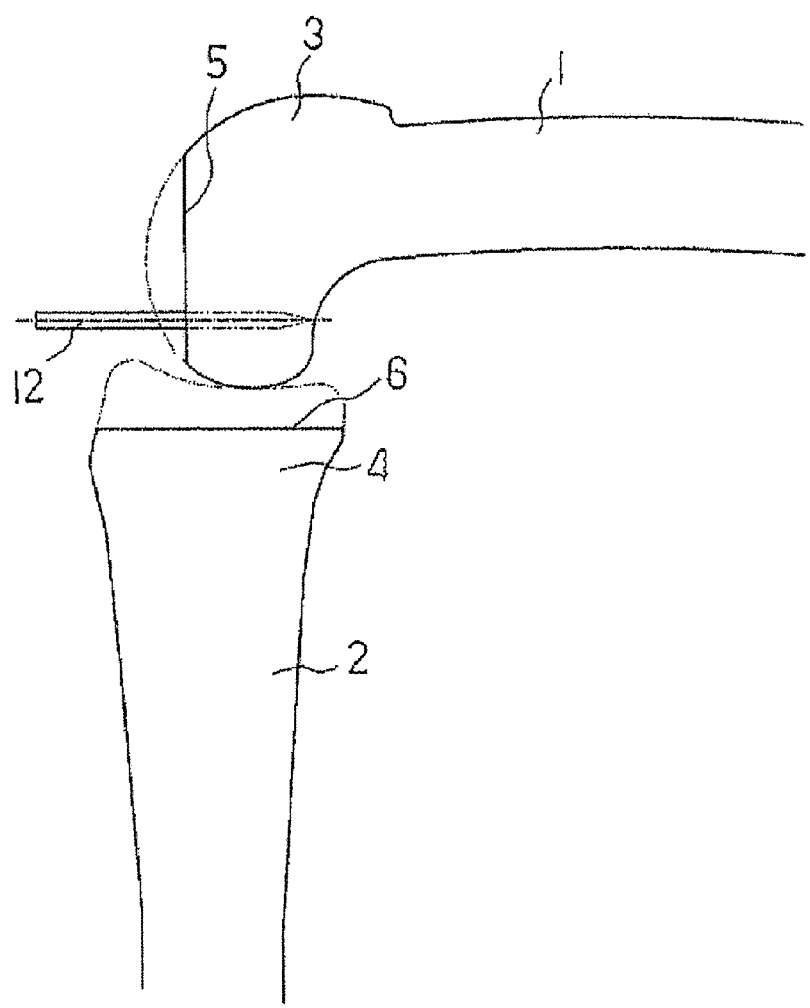
FIG. 9: Side view in which the femoral sizer is removed.

What is shown in FIG. 8 is called "femoral sizer" 13. The femoral sizer serves as a guide and aim for inserting pre-cut guide guide-pins 12, described below, which catches and holds the anterior and posterior parts of the condyles 3 of the femur 1 when the femur 1 is in a 90° flexed position. The vertical part of the femoral sizer 13 is fitted to the end resected surface 5 of the femur 1, and two insertion holes 14, parallel to each other on the left and right, are formed in this vertical part for inserting the pre-cut guide guide-pins 12 into the end resected surface 5. FIG. 9 shows a state after the femoral sizer 13 has been removed. In this state, the two pre-cut guide guide-pins 12, left and right, remain inserted. The pre-cut guide guide-pins 12 may have pointed tips to be directly pushed into the end resected surface 5; however, since this would have a risk to produce cracks, it is desirable that a hole-making instrument such as a drill (not shown in the drawing) be inserted into the insertion holes 14 to make holes in advance, and then the pre-cut guide guide-pins 12 be inserted into the holes formed by this instrument.

Figure 10:
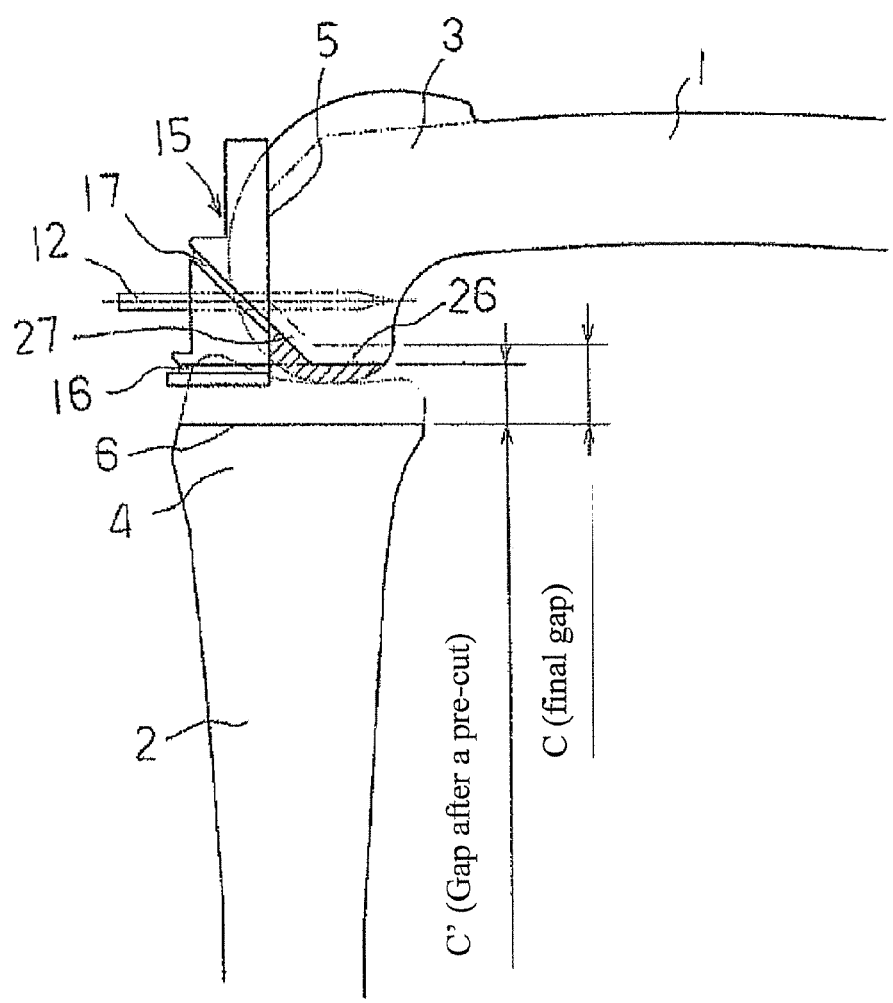
FIG. 10: Side view of a pre-cut guide.

FIG. 10 shows a "pre-cut guide" 15, and it is fitted to the end resected surface 5 using the pre-cut guide guide-pins 12 as a guide. The pre-cut guide 15 is an instrument that is fixed to the end resected surface 5, which is perpendicular to the condyle 3 (when the joint is in the 90° flexed position) and is used for chamfering the posterior part the edge connecting the posterior part and the end resected surface 5 of the condyle. An instrument for resecting the posterior part and the chamfered parts is inserted into the pre-cut guide 15, and therefore, this pre-cut guide 15 is formed therein with insertion holes 16 and 17 (more accurately, grooves having a certain width), which are, respectively, when the joint is in the flexed position, substantially horizontal and inclined downward, corresponding to the pre-cut line (actually, a surface). Instruments for resection are inserted into the insertion holes, and a posterior resected surface 26 and a posterior chamfer-resected surface 27 are formed thereby. In the shown example, the parts that are cut at this time (shown by diagonal lines) are made to leave (at least) an allowance with respect to a genuine-cut surface (a genuine-cut line), and this is called "pre-cut".

The reason for performing pre-cut is that, before the genuine implant is mounted, a pre-cut trial 19 (referred to below merely as a "trial"), described below, is mounted temporarily, and the gaps between the trial 19 and the end resected surface 6 of the tibia, when the joint is in the extended position and the flexed position and during the flexion, are measured. Moreover, this pre-cut is performed in order to observe the contact location of the trial 19 and the end resected surface 6, and the postures of the femur and tibia when the joint is in the extended and flexed positions; and also the contact location and the movement of the gravity center and posture of the trial 19 with respect to the end resected surface 6 during the flexion, etc. By doing this, it can be predicted whether or not the genuine implant, which is set-up in advance, and the genuine-cut line for mounting it are appropriate. If they are correct, then resections are performed accordingly, and the genuine implant set-up in advance is mounted; and if they are not correct, the genuine-cut line and the genuine implant are adjusted and modified.

Figure 11:
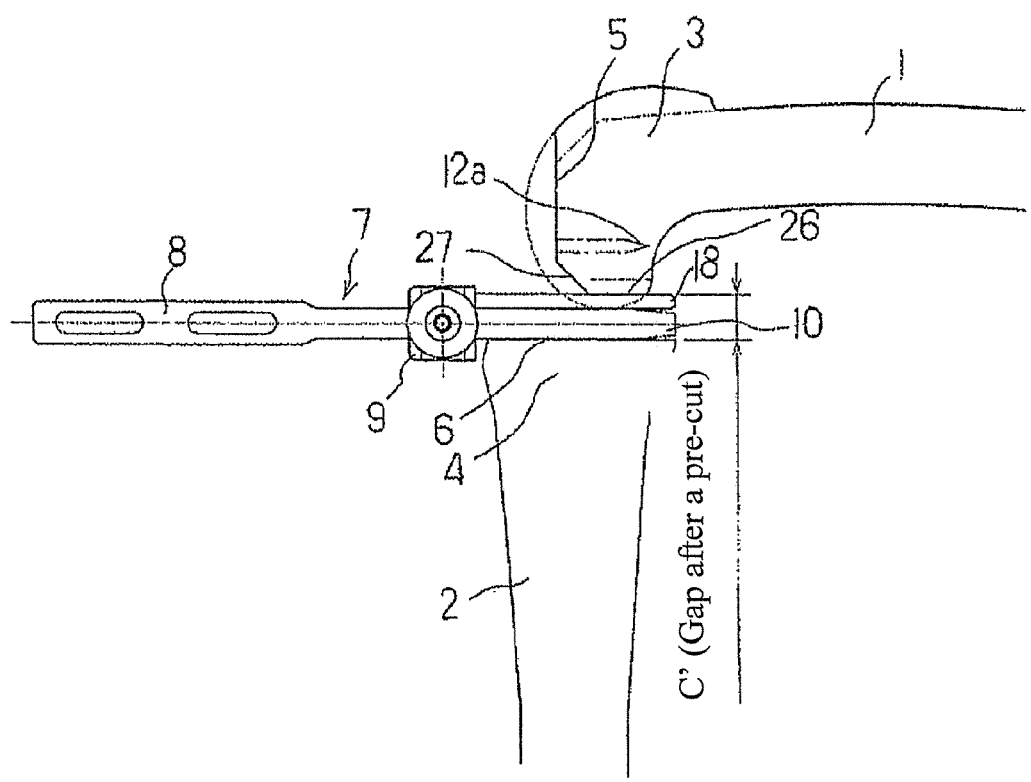
FIG. 11: Side view in which the spacer block inserted after the pre-cut guide is removed.

When the pre-cut is finished, the pre-cut guide guide-pins 12 are taken out (12a are the holes which are left); and as shown in FIG. 11, with the joint in a flexed position, the reference spacer part 10 of the spacer block 7 described above is inserted into the gap of the pre-cut range C'. This is done in order to verify whether the pre-cut range C' is correct when the femur is in a flexed position; and in order to measure this, an adjustment spacer 18 having a known thickness is set on the reference spacer part 10 of which thickness is also known (a plurality of adjustment spacers 18 can be used).

Figure 12:
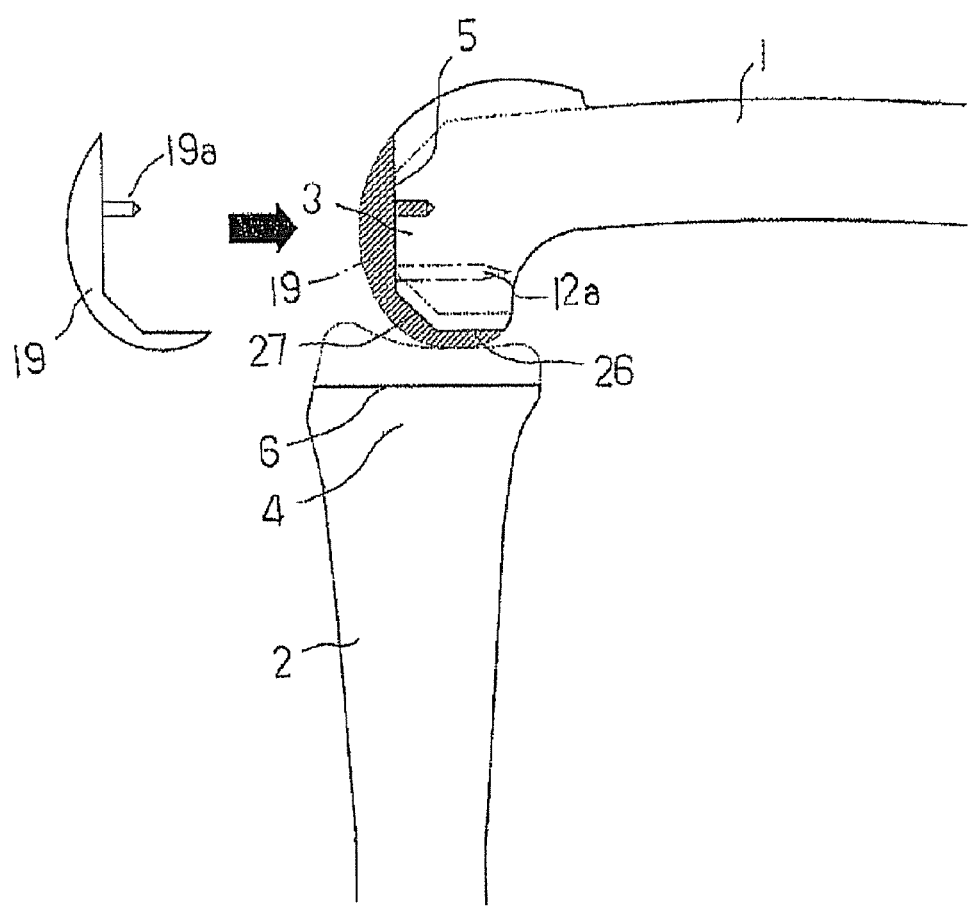
FIG. 12: Side view in which a pre-cut trial is mounted.

Next, as shown in FIG. 12, the trial 19 is mounted in the resection range C', covering the end resected surface 5, and the situations in the extended and flexed positions and the behavior while flexing is made are observed. The trial 19 is, via a small pin 19a, attached to and held by the end resected surface 5 of the condyle 3 formed by genuine-cut. The trial 19 is modeled to a genuine implant. However, since it is mounted in the pre-cut location, the parts fitted on the posterior resected surface 26 and the posterior chamfer-resected surface 27 are thinner than those of the genuine implant. The posterior resected surface 26 and the posterior chamfer-resected surface 27, to which pre-cut is performed, are generally parallel with these chamfer-resected surfaces 26 and 27, to which genuine-cut is performed.

Figure 13:
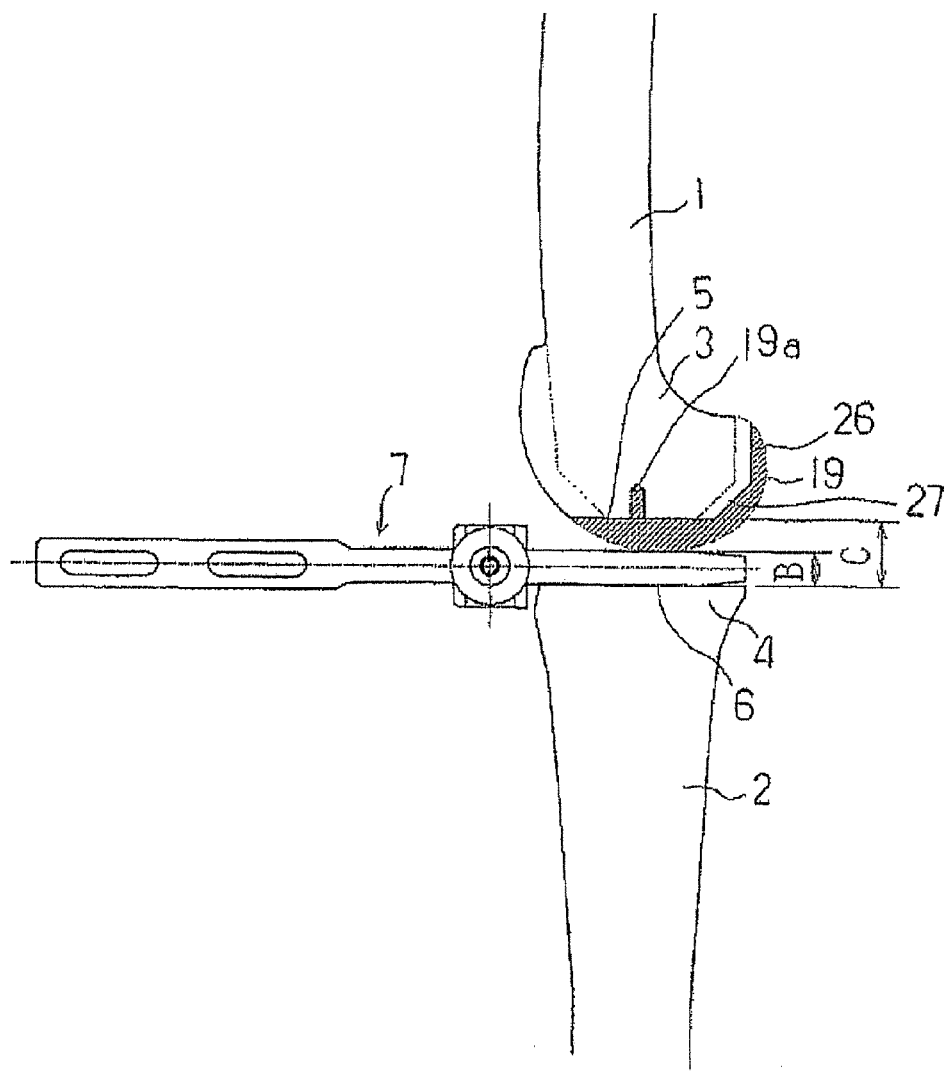
FIG. 13: Side view in extended position with the pre-cut trial mounted.
Figure 14:
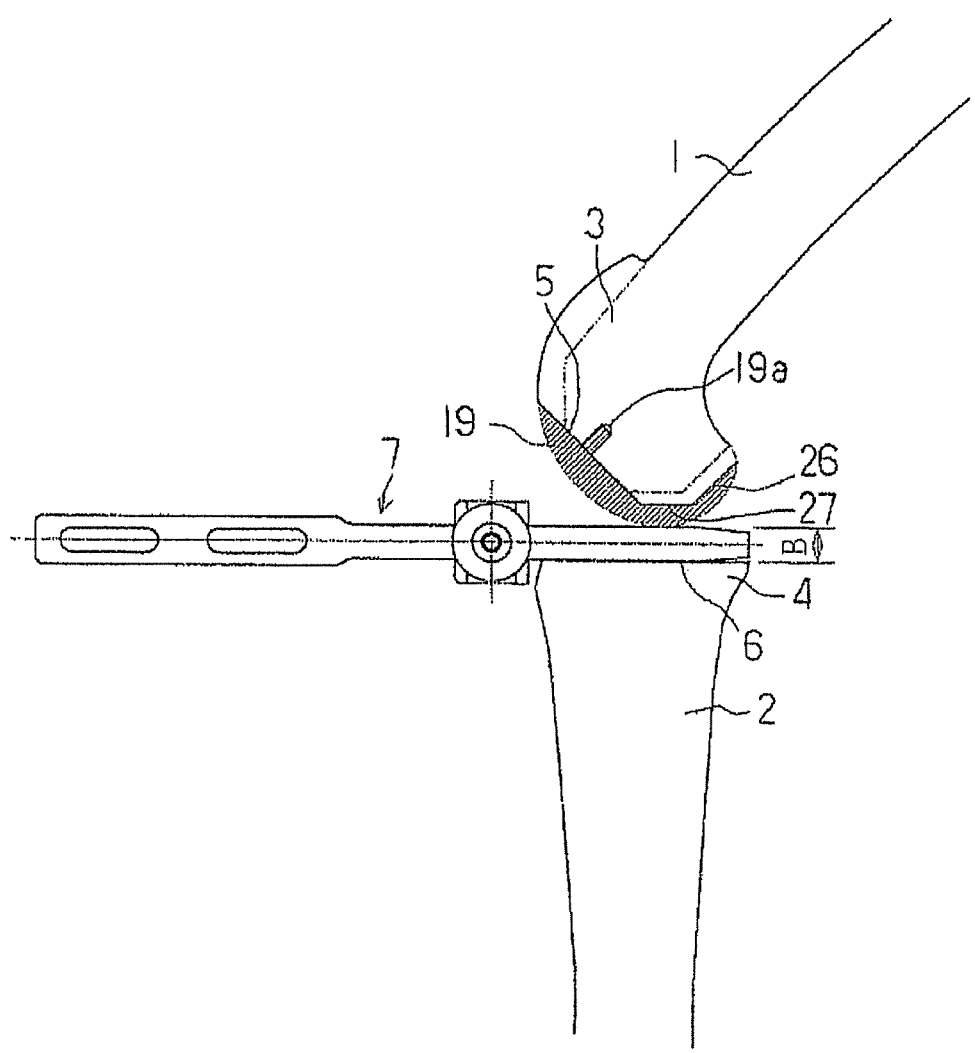
FIG. 14: Side view when rotated with the pre-cut trial mounted.
Figure 15:
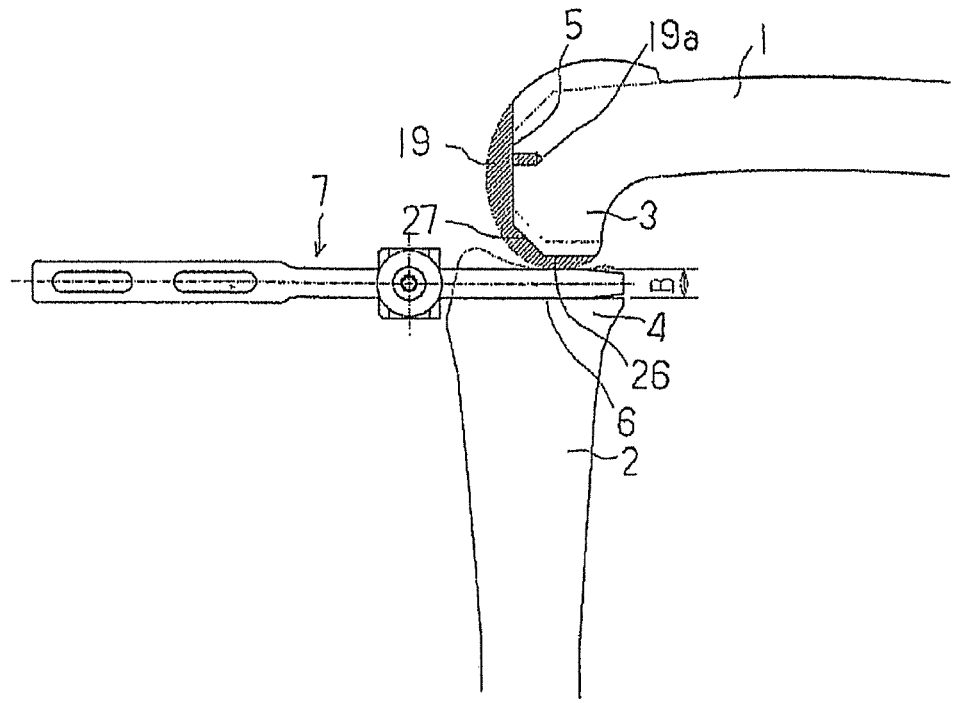
FIG. 15: Side view in which the pre-cut trial is mounted in flexed position.
Figure 16:
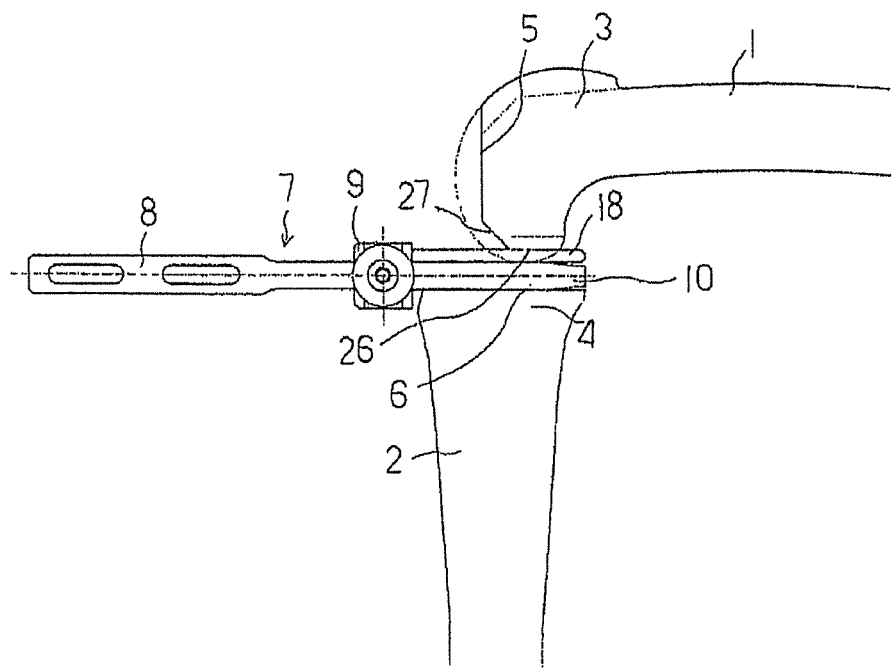
FIG. 16: Side view in which the spacer block is inserted after pre-cutting.

When the trial 19 is mounted, the adjustment spacer 18 is removed. First, the femur 1 is put in the extended position and then rotated until it reaches the flexed position, and the gap during this process is measured. The process of this flexion can be observed by radioscopy. As shown in FIGS. 13 to 15, the gap in the flexed position is smaller than the gap C in the extended position, but it becomes almost equal gap B until the flexed position is reached. The trial 19 is removed, and the lines (levels) of the posterior resected surface 26 and the posterior chamfer-resected surface 27 are re-checked further using the spacer block 7 and the adjustment spacer 18. This is done in order to verify whether any change has been produced in the pre-cut line due to the trial 19 that is mounted. FIG. 16 shows this verification in the flexed position.

Figure 17:
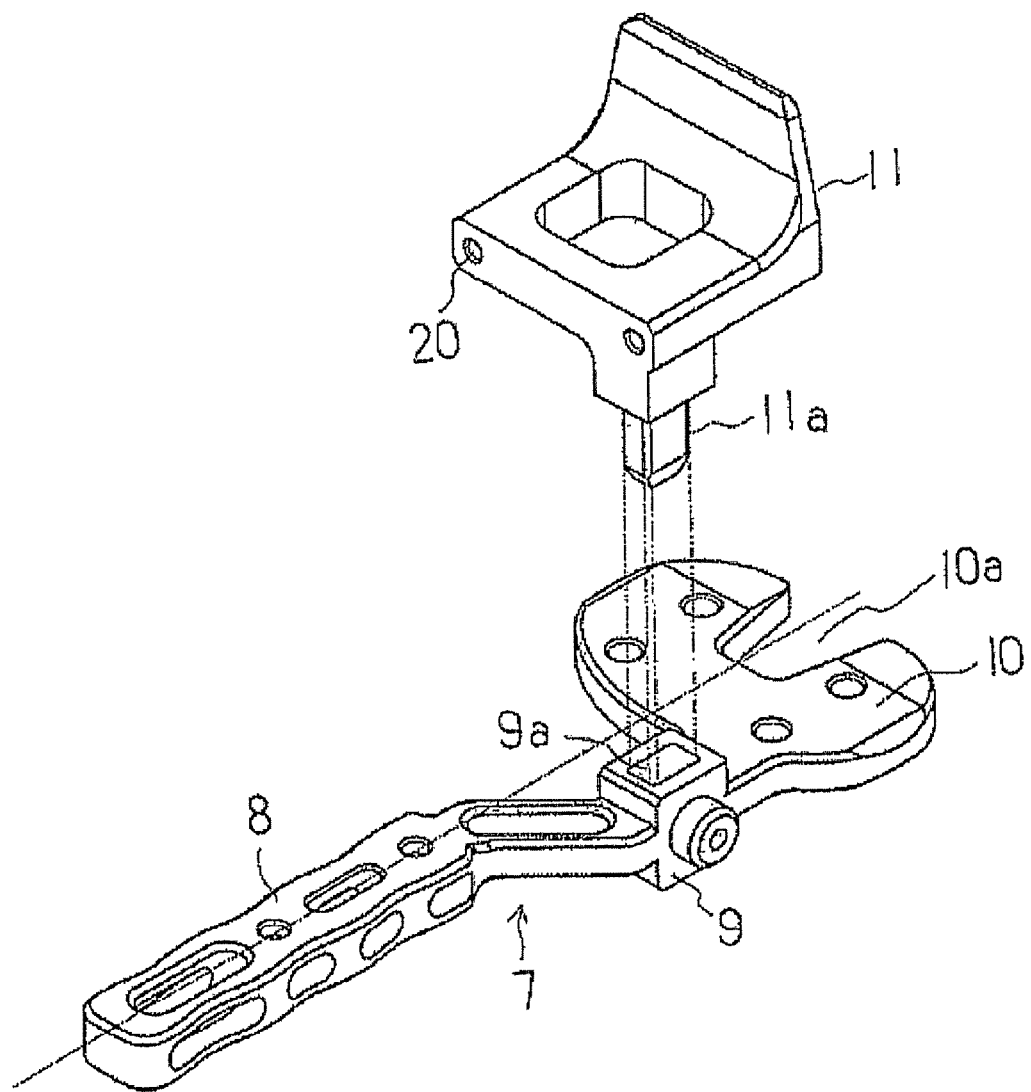
FIG. 17: Perspective view of a genuine-cut guide-pin guide.
Figure 18:
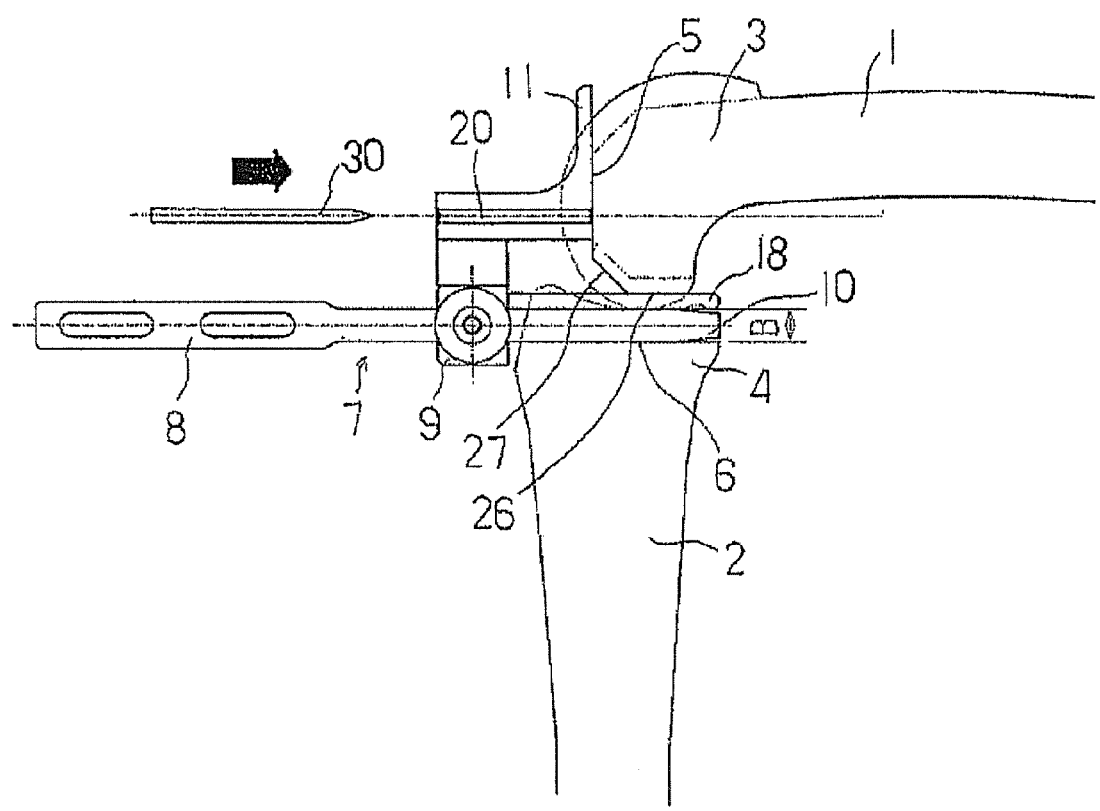
FIG. 18: Side view in which the genuine-cut guide-pin guide is mounted.

Next, the genuine-cut pin guide 11 described above is used while the joint is still in the flexed position. FIG. 17 is a perspective view of the genuine-cut pin guide 11. In FIG. 17, the leg 11a of the pin guide 11 is inserted and supported in the vertical hole 9a formed in the hollow box 9 of the above-described spacer block 7. The genuine-cut pin guide 11 has a part that comes into contact with the end resected surface 5 of the femur 1, and an insertion holes 20 are formed in that part. The insertion holes 20 are used for inserting the genuine-cut guide guide-pins (below referred to as the "genuine-cut pin") 30, which are for guiding the genuine-cut pin guide 11, into the end resected surface 5. As shown in FIG. 18, the genuine-cut pins 30 are inserted into the end resected surface 5 through the insertion holes 20.

In this case, the genuine-cut pins 30 can be the same as the pre-cut guide guide-pins 12; however, it is preferable that the locations where the they are inserted are different. This is because the pre-cut guide guide-pin holes 12a are sometimes enlarged by the use of the pre-cut guide guide-pins 12, and therefore there is a risk that the fixing of a genuine-cut guide 21, described below, will not be sufficient. Moreover, the partial interference of the genuine-cut pins 30 with the pre-cut guide guide-pin holes 12a would also cause risks of center displacement, which is not desirable.

More specifically, since the pre-cut is performed primarily on the posterior side, the pre-cut guide-pins 12 which guide the pre-cut guide 15 are also inserted in the posterior side; however, since the genuine-cut is performed on the anterior side as well, the load applies over a wide range of area; and thus the genuine-cut pins 30 are set more toward the center of the condyle 3 than the pre-cut guide guide-pin holes 12a. Moreover, similar to the pre-cut guide guide-pins 12, it is also more suitable, rather than direct insertion, to make holes 30a preliminarily with an instrument and then insert the genuine-cut pins 30 into this instrument hole. This will be discussed later.

Figure 19:
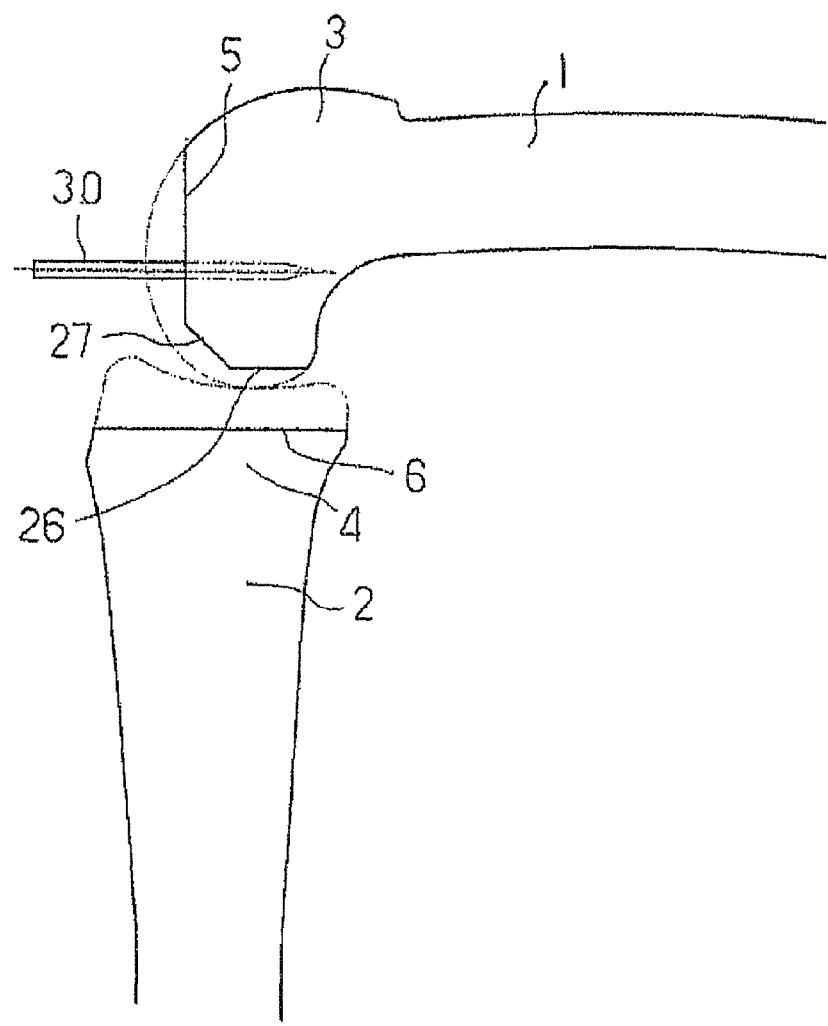
FIG. 19: Side view in which the genuine-cut guide-pin guide is removed.
Figure 20:
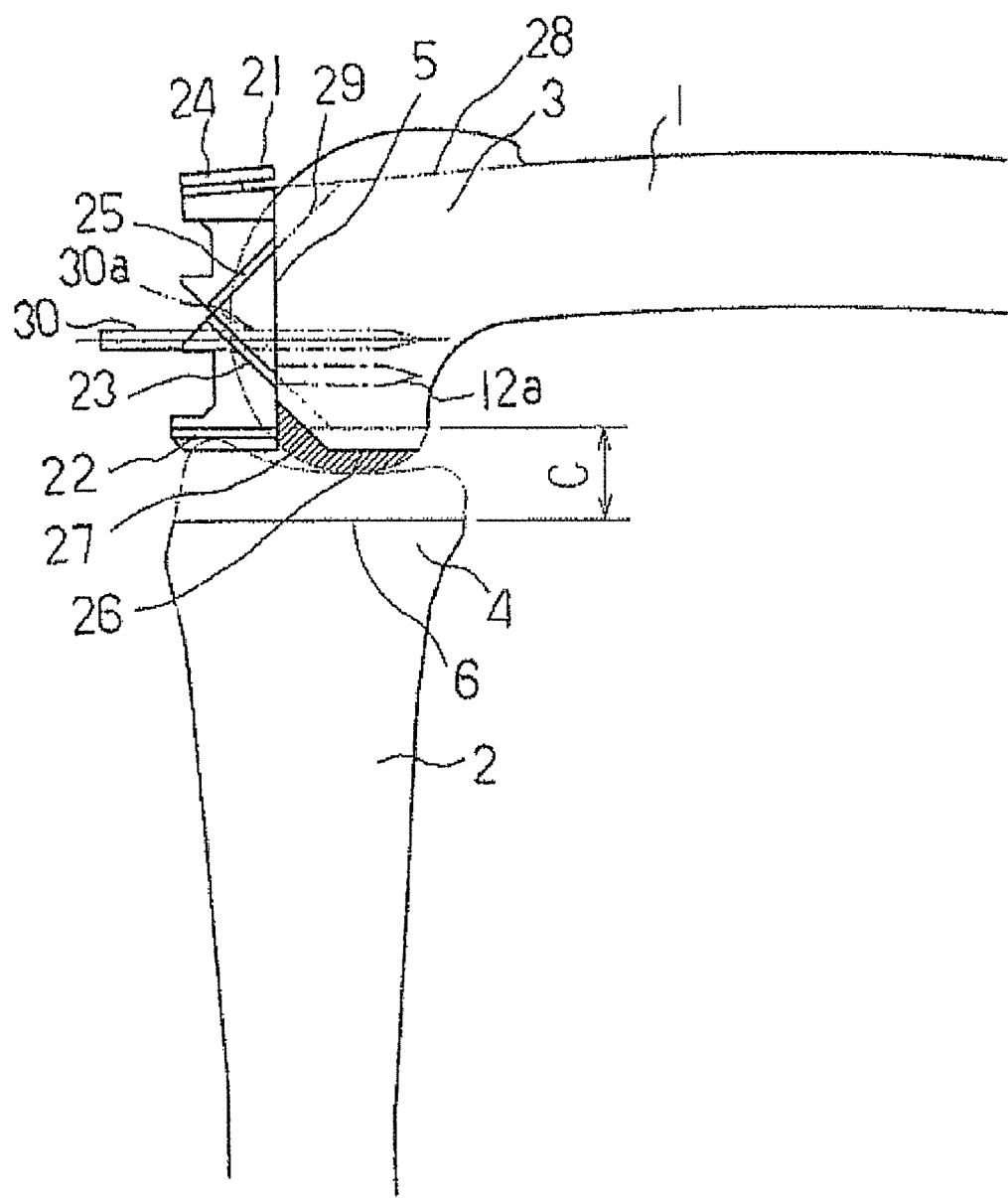
FIG. 20: Side view in which a genuine-cut guide is mounted.

Next, the spacer block 7 is pulled back, and the genuine-cut pin guide 11 is removed. When this is done, the genuine-cut pins 30 remain as shown in FIG. 19. The genuine-cut guide 21 is, accordingly, set by using the genuine-cut pins 30 as a guide. FIG. 20 shows this situation. The genuine-cut guide 21 is mounted by way of using the genuine-cut pins 30 as a guide, and it has a part that is fitted to the end resected surface 5. The genuine-cut guide 21 is an instrument for determining the genuine-cut line. The genuine-cut guide 21 is, therefore, provided with insertion holes (grooves having a certain width in the transverse direction; same in the below) 22 and 23 that respectively extend substantially horizontally and inclined downward, so that an instrument for forming the posterior resected surface 26 and the posterior chamfer-resected surface 27 is inserted. The genuine-cut guide 21 is also used to chamfer the anterior part and the edge connecting the anterior part and the end resected surface 5 to form an anterior resected surface 28 and an anterior chamfer-resected surface 29. Insertion holes 24 and 25 are accordingly further formed in the genuine-cut guide 21 in the same manner as described above regarding the insertion holes 22 and 23.

Figure 21:
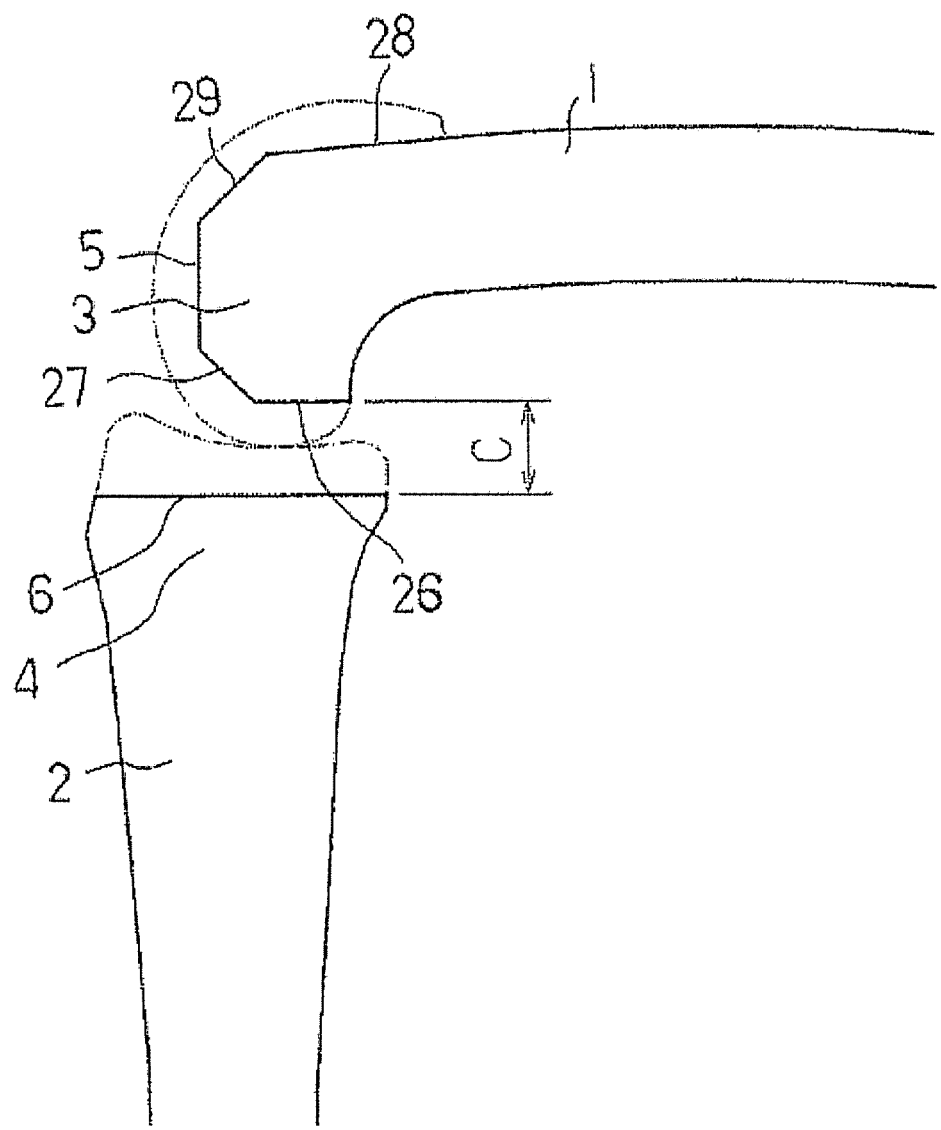
FIG. 21: Side view in which the genuine-cut guide is removed.

An instrument is inserted into the insertion holes 22 to 25, and cutting is performed along the respective genuine-cut lines. FIG. 21 shows this situation. When the genuine-cut is completed, the end resected surface 5, the posterior resected surface 26, the posterior chamfer-resected surface 27, the anterior resected surface 28, and the anterior chamfer-resected surface 29 faun a pentagon when viewed from the side (it can be formed in a polygon having more sides). The genuine-cut guide 21 is taken out, and the genuine-cut pins 30 are removed as well, and then the genuine implant (not shown in the drawing) which has been set-up or adjusted is mounted there.

A tibial side genuine implant (not shown in the drawing) is mounted likewise on the articular surface 4 of the tibia 2. As is well known, an ultra-high-molecular-weight polyethylene articular surface is attached on a tibial articular member which is mounted on the end resected surface 6 of the afflicted part of the tibia 2.

As seen from the above, the present invention is characterized primarily by the fact that, the gap and the clearance of the extended and flexed positions and during behavior of flexing, are observed on the femoral side as well as on the posterior side of the condyle 3 of the femur 1 which function when flexion is performed, and the situation when the trial 19 is used is observed, and then the genuine-cut line and the genuine implant are determined and adjusted. Accordingly, the genuine implant can be mounted in the most appropriate manner.

The basic form of the present invention is as described above, and it can take various modified forms as long as the essential nature is preserved. The gist of the modifications below is to make the trial 19 in a form close to genuine implants as much as possible and to be able to comply with minimal-invasion operations, which have been recently performed, in view of the fact that the size of incision and the area of the incision vary depending on operators who take the degrees of the various injuries to patients' bones into consideration.

Figure 22:
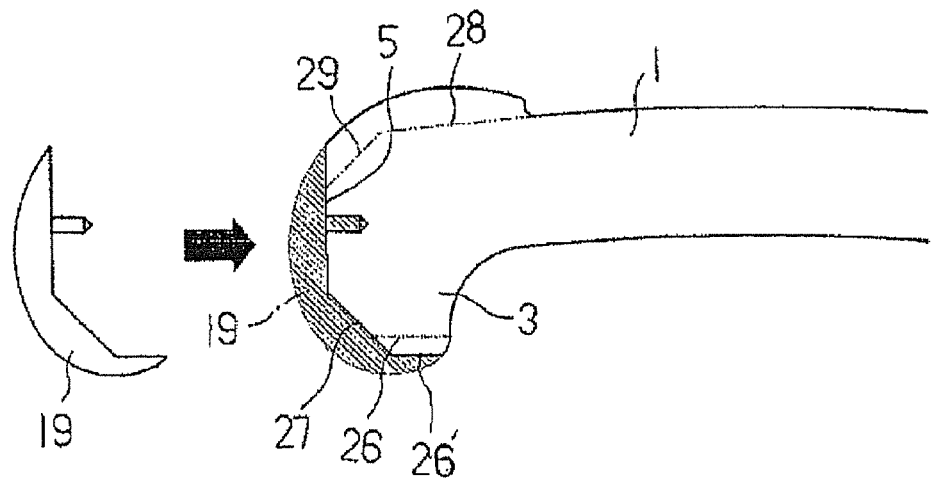
FIG. 22: Explanatory drawing of another example of the pre-cut trial.

FIG. 22 shows a case in which the degree of injury to the posterior part is low; and the end resected surface 5 and the posterior chamfer-resected surface 27 are genuine-cut, and the posterior resected surface 26 is made posterior resected surface 26' which is pre-cut shallowly (in the below, apostrophe (') is added to each of the numbers referred in the above to the genuine-cut line in order to distinguish the pre-cut line from the genuine-cut line), and the trial 19 is mounted on these surfaces.

Figure 23:
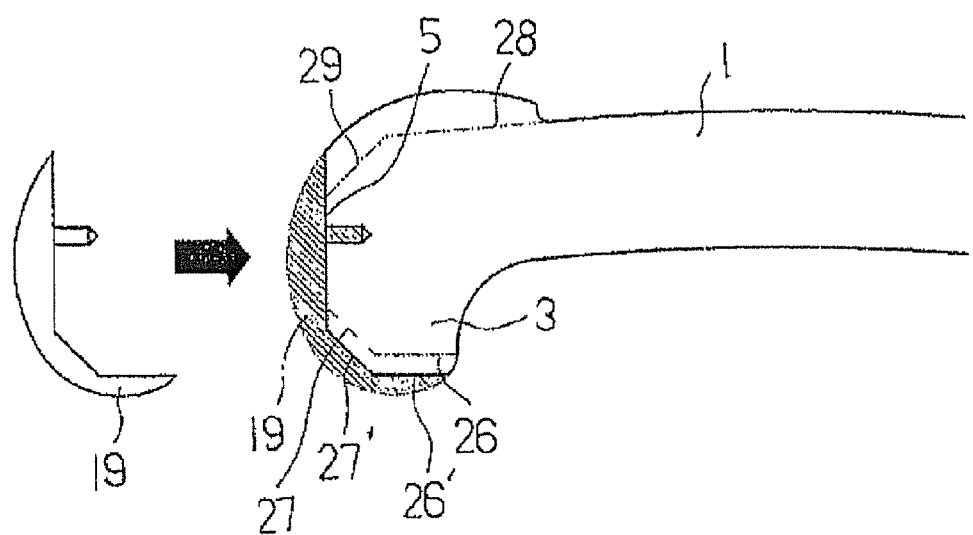
FIG. 23: Explanatory drawing of another example of the pre-cut trial.

FIG. 23 shows a similar case, wherein the posterior chamfer-resected surface 27 and the posterior resected surface 26 are formed by cutting posterior part of the condyle of the femur shallowly so as to be, respectively, a posterior chamfer-resected surface 27' and a posterior resected surface 26', which are thus respectively forming pre-cut lines; and the trial 19 is formed so as to be mounted on these surfaces.

Figure 24:
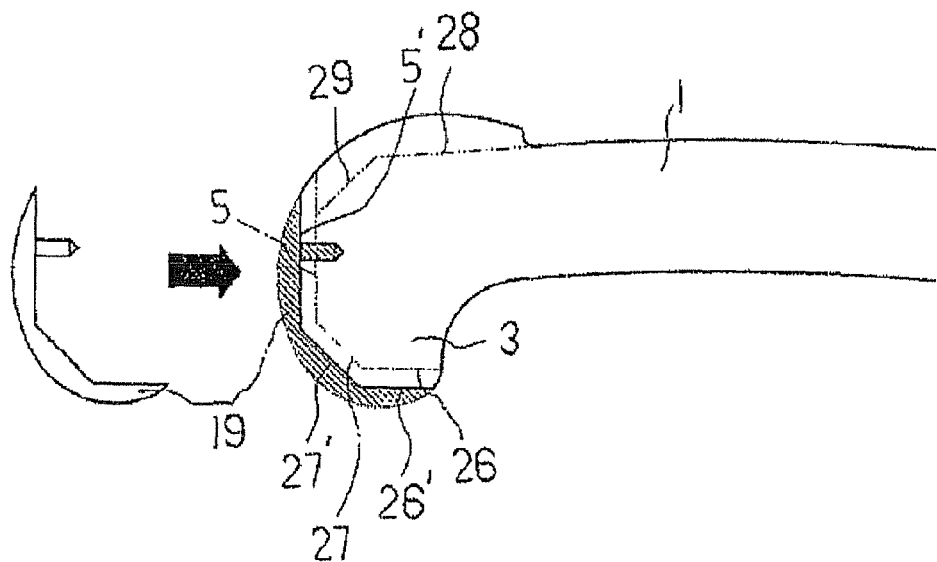
FIG. 24: Explanatory drawing of another example of the pre-cut trial.

In FIG. 24, the end resected surface 5, the posterior chamfer-resected surface 27, and the posterior resected surface 26 are formed by cutting the condyle of the femur shallowly so as to respectively make an end resected surface 5', a posterior chamfer-resected surface 27', and a posterior resected surface 26', which are thus respectively forming pre-cut lines; and the trial 19 is formed so as to be mounted on these surfaces.

Figure 25:
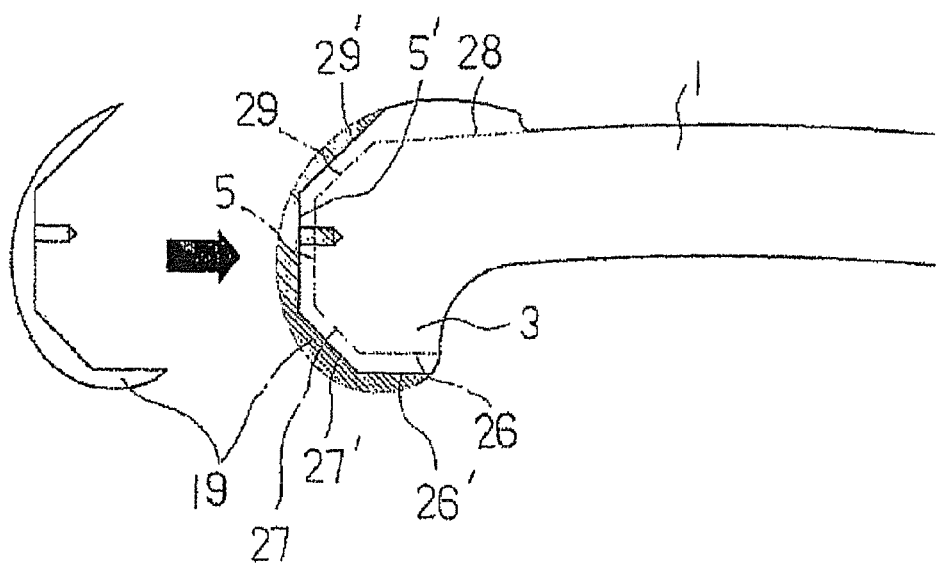
FIG. 25: Explanatory drawing of another example of the pre-cut trial.
Figure 26:
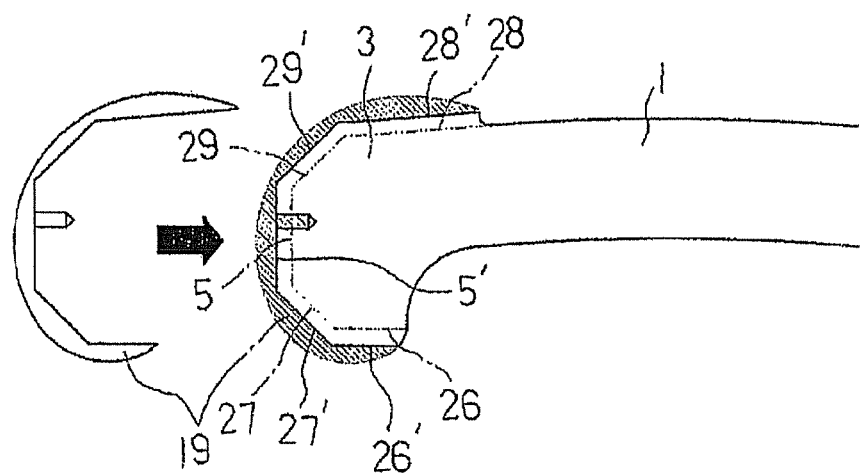
FIG. 26: Explanatory drawing of another example of the pre-cut trial.
Figure 27:
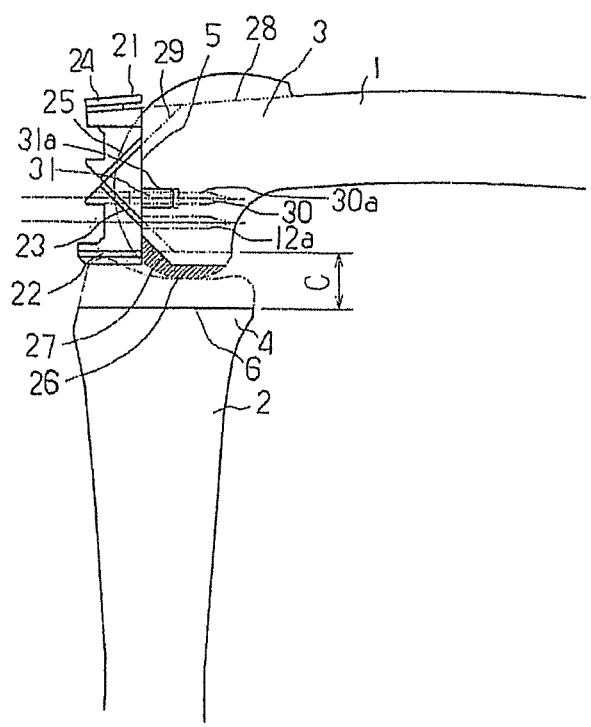
FIG. 27: Side view in which another example of the genuine-cut guide is mounted.

In FIG. 25, the trial 19 extends to the anterior side of the femur when the degree of injury to the condyle 3 is low. The anterior chamfer-resected surface 29 is formed by cutting anterior part of the condyle of the femur shallowly so as to be an anterior chamfer-resected surface 29' that forms the pre-cut line; and the trial 19 is formed so as to extend to this surface. FIG. 26 shows the case in which the prior structure is further enlarged. The anterior resected surface 28 is cut shallowly so as to make a chamfer-resected surface 28a of pre-cut line, and the trial 19 is formed so further extend to this surface. Although the trial 19 in this case is thin as a whole, it is made substantially the same shape as a genuine implant, and it is further closer to a genuine implant.

Besides these modifications, there are still more various possible combinations of the shape of the trial 19 and the end resected surface 5', the posterior chamfer-resected surface 27', the posterior resected surface 26', the anterior chamfer-resected surface 29', and the anterior resected surface 28' which become the pre-cut lines on which the trial is mounted although the drawings for these are omitted. The necessary conditions for such combinations are: if the end resected surface 5 is defined by a genuine-cut line, at least one of the other surfaces is a pre-cut line; and, if the end resected surface 5 is defined by a pre-cut line, then other surfaces are genuine-cut lines or pre-cut lines.

Furthermore, as to the method for inserting the above-described genuine-cut pins 30 into the insertion holes 20 formed in advance, a conceivable method is to use the insertion holes 20 of the genuine-cut pin guide 11. More specifically, it is the method that a hole-making instrument such as a drill is inserted through the insertion holes 20, and holes are made thereby in the end resected surface 5, and then sleeves 31, in which holes are made through which the genuine-cut pins 30 can be inserted, are put into the holes thus made, and the sleeves 31 are inserted in the instrument hole. In this case, such a method can be employed that the holes 31a into which the sleeves 31 are inserted are made deep enough so that the sleeves 31 are inserted, and then the genuine-cut pins 30 are directly driven in. Another method is to form in advance holes 30a as well that allows the genuine-cut pins 30 to be inserted.

The latter method is superior since there is little damage to the bone; however, the drawback is that holes must be made twice. Therefore, if a two-stage drill, etc., appropriate for making both holes 31a and 30a at the same time is used, only one hole-making operation is needed. If this is done, pre-cut guide guide-pins 12 and genuine-cut pins 30 of different diameters or lengths can be used. Accordingly, such an effect, for example, is obtainable that the genuine-cut pins 30 can be made larger than the diameter of pre-cut guide guide-pins 12, thus allowing the fixing of the genuine-cut guide 21, which generally applies load over a wider area, to be more stable.

In the technique described above, after the trial 19 is mounted and the gap from the extended position to the flexed position is measured and also the state of the rotation is observed, the trial 19 is removed and the gap is measured again. However, in some cases, this operation can be omitted. If the degree of bone damage is not very severe, there is almost no difference between these two measurements; and as a result, such measurement steps can be omitted, which the advantage that the operation time can be shortened.

The invention claimed is:

1. A surgical instrument comprising:
   a pre-cut trial configured to be mounted during an artificial knee joint replacement operation on a resected surface of a pre-cut line cut shallower than a genuine cut line by a pre-cut trial pin configured to be inserted in the resected surface, so that extension and flexion of femur and tibia can be observed and that it can be judged whether or not a genuine implant is appropriate,
   a pre-cut guide configured to be mounted on the end resected surface defined by the genuine-cut line or the pre-cut line;
   a femoral sizer configured to be seated in and fitted to anterior and posterior condyles of the femur;
   a pre-cut guide guide-pin configured to be inserted in the end resected surface through an insertion hole formed in the femoral sizer; and
   a resection instrument configured to be inserted from the insertion hole, wherein
   the resected surface comprises an end resected surface, which is perpendicular to a bone axis, posterior and anterior resected surfaces, which are parallel to the bone axis, a posterior chamfer-resected surface connecting the end resected surface and the posterior resected surface, and an anterior chamfer-resected surface connecting the end resected surface and the anterior resected surface;
   said pre-cut trial is configured to be mounted on part or all of said genuine-cut line or part or all of said pre-cut line; and
   at least the posterior chamfer-resected surface and posterior resected surface are formed by performing genuine-cut or pre-cut by inserting the resection instrument into the insertion hole.

2. A surgical instrument according to claim 1, wherein
   the pre-cut trial is configured to be mounted on the end resected surface defined by the genuine-cut line and
   the pre-cut trial is configured to be mounted on at least one of the posterior chamfer -rsected surface, the posterior resected surface, the anterior chamfer-resected surface and the anterior resected surface; and among said surfaces, at least one is the pre-cut line.

3. A surgical instrument according to claim 1, wherein
   the pre-cut trial is configured to be mounted on the end resected surface defined by the pre-cut line and
   the pre-cut trial is configured to be mounted on at least one of the posterior chamfer-resected surface, the posterior resected surface, the anterior chamfer-resected surface and the anterior resected surface of the genuine-cut line or the pre-cut line.

4. A surgical instrument according to claim 1, wherein the pre-cut guide has an insertion hole configured such that a resection instrument for cutting the anterior chamfer-resected surface and anterior resected surface is insertable therethrough to perform genuine-cut or pre-cut.

5. A surgical instrument according to claim 1, comprising:
a genuine-cut guide configured to be mounted on the end resected surface;
a spacer block configured to be inserted, after the pre-cut trial guide is mounted and states in the extended and flexed positions and a flexing state are observed, between the end resected surface of the genuine-cut line or the pre-cut line and the end resected surface of the tibial side;
a genuine-cut guide guide-pin configured to be inserted into the end resected surface through an insertion hole of the genuine-cut guide and to guide the genuine-cut guide to be fixed to the end resected surface, wherein
the genuine-cut guide is configured to be attached to the spacer block and fitted to the end resected surface of the genuine-cut line or pre-cut line, and
the resection instrument is configured to be inserted through the insertion hole so as to perform genuine-cut.

6. A surgical instrument according to claim 5, wherein
the insertion hole of the genuine-cut guide guide-pin guide is a hole into which a hole-making instrument, such as a drill, can be inserted,
the genuine-cut guide has a sleeve configured to be inserted in an instrument hole formed by the hole-making instrument and has a hole into which the genuine-cut guide guide-pin is configured to be inserted, and
the genuine-cut guide is configured to be fixed to the end resected surface which is formed by genuine-cut or pre-cut using the sleeve.

7. A surgical instrument according to claim 6, wherein
the insertion hole of the femoral sizer is one into which the hole-making instrument can be inserted, and
the pre-cut guide-pin is configured to be inserted into the instrument hole formed by the hole-making instrument.

* * * * *